US009456633B2

(12) United States Patent
Liu

(10) Patent No.: US 9,456,633 B2
(45) Date of Patent: Oct. 4, 2016

(54) ATOMIZING DEVICE AND ELECTRONIC CIGARETTE USING THE SAME

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 668 days.

(21) Appl. No.: 13/992,736

(22) PCT Filed: Dec. 14, 2012

(86) PCT No.: PCT/CN2012/086685
§ 371 (c)(1),
(2) Date: Jun. 8, 2013

(87) PCT Pub. No.: WO2013/149484
PCT Pub. Date: Oct. 10, 2013

(65) Prior Publication Data
US 2014/0060524 A1    Mar. 6, 2014

(30) Foreign Application Priority Data

Apr. 1, 2012   (CN) .......................... 2012 2 0141170
Jun. 5, 2012   (WO) ................ PCT/CN2012/076492
Jun. 5, 2012   (WO) ................ PCT/CN2012/076493

(51) Int. Cl.
*A61M 11/00*   (2006.01)
*A24F 7/00*    (2006.01)
*A61M 15/06*   (2006.01)
*A24F 47/00*   (2006.01)
*H05B 3/02*    (2006.01)
*H05B 3/03*    (2006.01)

(Continued)

(52) U.S. Cl.
CPC ............. *A24F 47/008* (2013.01); *A61M 11/00* (2013.01); *A61M 11/041* (2013.01); *A61M 11/042* (2014.02); *A61M 15/06* (2013.01); *A61M 16/06* (2013.01); *H05B 3/026* (2013.01); *H05B 3/03* (2013.01)

(58) Field of Classification Search
CPC .. A61M 15/06; A61M 11/042; A61M 11/00; A24F 47/008; A24F 47/002; A24F 47/004
USPC ................................................ 439/271, 587
See application file for complete search history.

(56) References Cited

U.S. PATENT DOCUMENTS 3,518,358 A * 6/1970 Brown ................. H02G 15/043
                                                174/138 F
6,558,180 B2 * 5/2003 Nishimoto ......... H01R 13/5221
                                                439/271

(Continued)

*Primary Examiner* — Justine Yu
*Assistant Examiner* — Douglas Sul
(74) *Attorney, Agent, or Firm* — Cheng-Ju Chiang

(57) ABSTRACT

The present invention provides an atomizing device and an electronic cigarette using the same. The atomizing device includes an outer sleeve, a liquid storage layer, a heating assembly, an atomizing elastic seat and a hard connecting assembly. The hard connecting assembly is inserted in the atomizing seat to elastically squeeze and tensioningly engage. The atomizing seat is adapted for the outer sleeve, and elastically expanded as a result of the connecting assembly being inserted in the elastic atomizing seat to be tightly sealed in the inner wall of the outer sleeve. The electronic lines are respectively tensioningly fixed in the elastic atomizing seat and electrically connect to the connecting assembly. The strength of the atomizing device is highly enhanced and assures further assembly. The atomizing seats is squeezed and sealed by the connecting head.

14 Claims, 5 Drawing Sheets

(51) Int. Cl.
   *A61M 11/04*   (2006.01)
   *A61M 16/06*   (2006.01)

(56) References Cited

U.S. PATENT DOCUMENTS

| | | | |
|---|---|---|---|
| 8,205,622 B2* | 6/2012 | Pan | A24F 47/008 131/273 |
| 2006/0191546 A1* | 8/2006 | Takano | A24F 47/002 131/270 |
| 2011/0303231 A1* | 12/2011 | Li | A24F 47/008 131/329 |
| 2012/0111347 A1* | 5/2012 | Hon | A24F 47/008 131/329 |
| 2012/0145169 A1* | 6/2012 | Wu | A24F 47/008 131/273 |
| 2012/0199663 A1* | 8/2012 | Qiu | A61M 11/041 239/8 |
| 2013/0192616 A1* | 8/2013 | Tucker | H01C 17/00 131/328 |

* cited by examiner

ATOMIZING DEVICE AND ELECTRONIC CIGARETTE USING THE SAME

CROSS REFERENCE TO RELATED APPLICATIONS

The present application is a 35 U.S.C. §371 National Phase conversion of International (PCT) Patent Application No. PCT/CN2012/086685, filed on Dec. 14, 2012, the disclosure of which is incorporated by reference herein. The PCT International Patent Application was filed in Chinese.

FIELD OF THE INVENTION

The present invention relates to atomizing devices, and more particularly pertains to atomizing devices of smoking simulators and electronic cigarette using the atomizing device.

BACKGROUND OF THE INVENTION

Current atomizer used in electronic cigarette generally uses absorbent cotton fixed on an atomizing seat. A heating wire is located in the absorbent cotton to heat tobacco flavored liquid. The electronic line of the heating wire needs to be welded to corresponding electrode. The current atomizer used in electronic cigarette has at least the following problems: the sealing of the atomizing seat for tobacco flavored liquid is not tight or balanced; the assembly of the atomizing device and the absorbent cotton is inconvenient; the operation of the heating wire is complicated, which easily makes welding poor, thus makes the atomizer out of work; welding residue is harmful to people.

SUMMARY OF THE INVENTION

An object of the present invention to provide an atomizing device which has good sealing, high strength, and easily assembled.

Another object of the present invention to provide a disposable electronic cigarette, in which atomizing device has good sealing, high strength, and easily assembled.

An additional object of the present invention to provide a reusable electronic cigarette, in which atomizing device has good sealing, high strength, and easily assembled.

To achieve the above object, the present invention provides an atomizing device comprising an outer sleeve, liquid storage layer, heating assembly, atomizing seat and hard connecting assembly. The liquid storage layer, the heating assembly and the atomizing seat are assembled in the outer sleeve. The atomizing seat is an elastic atomizing seat. The hard connecting assembly is inserted in the elastic atomizing seat to elastically squeeze and tensioningly engage with the elastic atomizing seat.

In a further embodiment, the elastic atomizing seat is adapted to the outer sleeve. The elastic atomizing seat is elastically expanded as a result of the connecting assembly being inserted in the elastic atomizing seat to be tightly sealed in the inner wall of the outer sleeve.

In a further embodiment, the heating assembly comprises heating element and electronic lines connected to two end of the heating element. The electronic lines respectively are tensioningly fixed in the elastic atomizing seat and electrically connect to the connecting assembly.

In a further embodiment, the connecting assembly comprises conductive connecting head and a top electrode. The conductive connecting head and the top electrode are insulatively engage with each other. The elastic atomizing seat defines slot. The conductive head is tensioningly inserted into the slot. The elastic atomizing seat defines air channel therein. The top electrode is inserted the air channel to tensioningly engage with the inner wall of the elastic atomizing seat.

In a further embodiment, the heating assembly comprises a heating element and electronic lines connected to two end of the heating element. One electronic line is tensioningly fixed between the elastic atomizing seat and the connecting head to electrically connect to the connecting head. The other electronic line is tensioningly fixed between the air channel wall of the elastic atomizing seat and the top electrode to electrically connect to the top electrode. The conductive connecting head is metallic.

In a further embodiment, the elastic atomizing seat comprises main body and axial extending portion formed on the center of the main body. The air channel of the atomizing seat runs through the main body and the axial extending portion. The main body forms an annular flange on an outer edge thereof. The outer diameter of the annular flange is adapted to an inner diameter of the outer sleeve, tightly latches the inner wall of the outer sleeve to achieve seal. The annular flange and the outer wall of the main body cooperatively restrict the slot.

In a further embodiment, the elastic atomizing seat forms a pair of line holes used for the electronic lines passing through. The line holes have thin neck. When the atomizing seat is squeezed, the thin neck elastically deforms to tightly clamp the electronic lines therein.

In a further embodiment, the line holes longitudinally pass through the main body of the elastic atomizing device. One line hole communicates with the air channel. One electronic line passes through a corresponding line hole and bypasses a bottom edge of the main body to stretch into the slot and is latched in the inner wall of the slot by the connecting head. The other electronic line passes through the other corresponding line hole to go back the inner wall of the air channel and is clamped by the top electrode.

In a further embodiment, the outer wall of the connecting head forms an annular flange adapted to the inner diameter of the outer sleeve. The connecting head forms a stepped hole therein. When the connecting head is inserted into the slot, the annular flange of the connecting head longitudinally resists the annular flange of the atomizing seat. The main body the atomizing seat is tensioningly latched in the stepped hole of the connecting head. The top electrode is latched the stepped hole of the connecting head via an insulating ring, and longitudinally extending and tensioningly latches in the inner wall of the air channel of the main body of the atomizing seat.

In a further embodiment, the atomizing device further comprises glass fiber tube. The glass fiber tube defines assembling hole to fix the heating assembly. The glass fiber tube may be double layer tube. An inner layer tube forms a supporting ear corresponding to the assembling hole to fix the heating assembly. The elastic atomizing seat is made of silicon.

In a further embodiment, the liquid storage layer is a storage cotton packaging on the outer of the glass fiber tube.

In a further embodiment, the glass fiber tube packaged by a cloth layer, and then is packaged by the storage cotton.

The present invention further provides a disposable electronic cigarette comprising the above-mentioned atomizing device, and further comprising battery assembly. The positive and negative electrodes respectively electrically connect with the connecting assembly.

In a further embodiment, the battery assembly is assembled in the outer sleeve.

The present invention further provides a reusable electronic cigarette comprising the above-mentioned atomizing device, and further comprising a power source pole. The power source pole connects with the atomizing device. The positive and negative electrodes of the power source pole respectively electrically connect with the connecting assembly.

The atomizing device and the electronic cigarette of the present invention has the following advantage: the strength of the atomizing seat covered by the connecting head or other related elements is greatly enhanced to ensure assembly convenient; avoiding an user's hand hold inconvenient to package cotton and too soft of the simply using silicon glue; avoiding leaking liquid, plugging holes as results of easy deflection. The atomizing seats is squeezed and sealed by the connecting head, of which sealing is better and avoid too soft of the simply using silicon glue, and also avoid inconvenient to assembly when a simple sealing ring moves with the atomizing sleeve assembling in. After assembling the atomizing seat of the heating assembly and the connecting head together, hand only holds the connecting head to package cotton, in which efficiency and yield are greatly improved. The electronic lines are not required to weld, which avoids all poor phenomenon.

The components in the drawings are not necessarily drawn to scale, the emphasis instead being placed upon illustrating the principles of the present disclosure. Moreover, in the drawings, like reference numerals designate corresponding parts throughout several views, and all the views are schematic.

DETAILED DESCRIPTION OF THE INVENTION

It is needed to state that embodiments and all element limitations in all embodiments may be combined in the case of no conflicts. The present invention will be described in detail in the following combining figures and embodiments.

Figure 1:
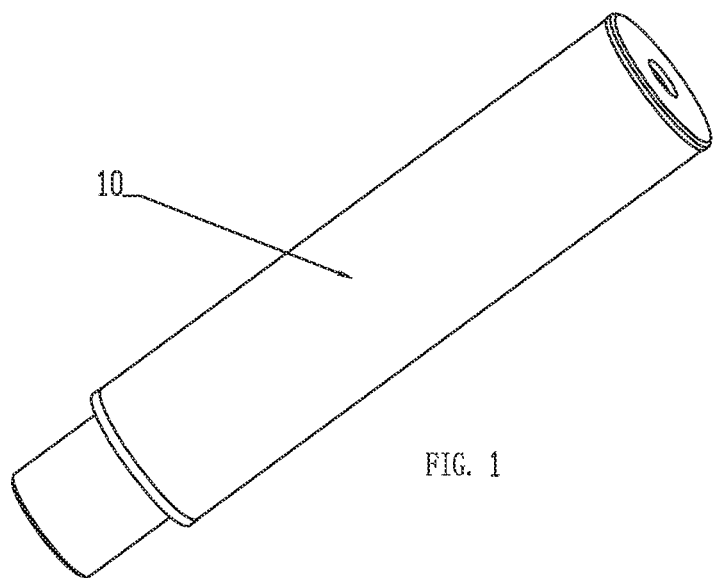
FIG. 1 is a perspective view of the atomizing device according to an embodiment of the present invention.
Figure 2:
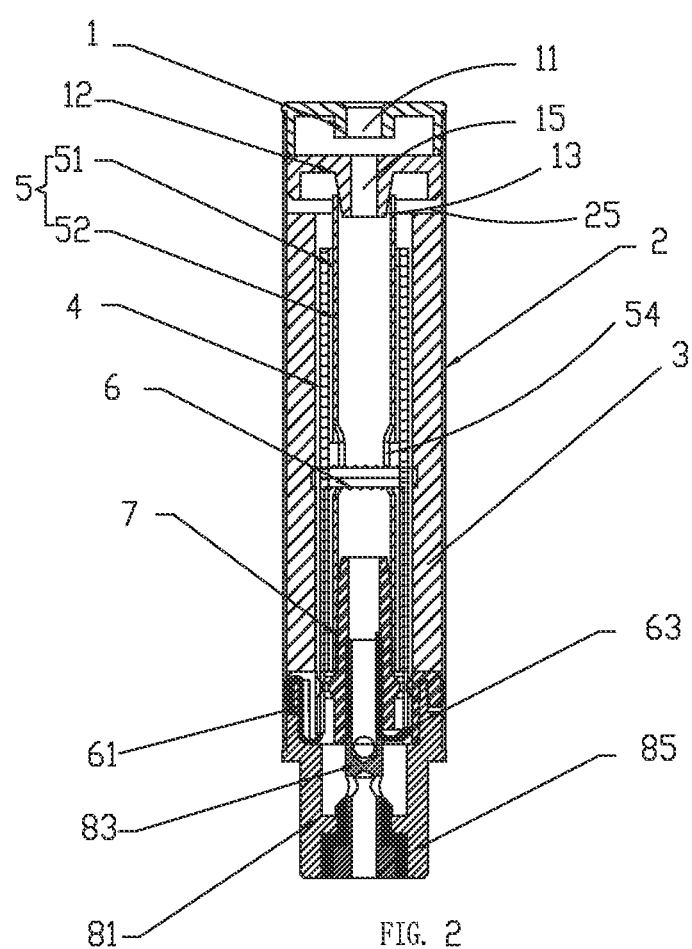
FIG. 2 is a sectional view of the atomizing device according to an embodiment of the present invention.
Figure 3:
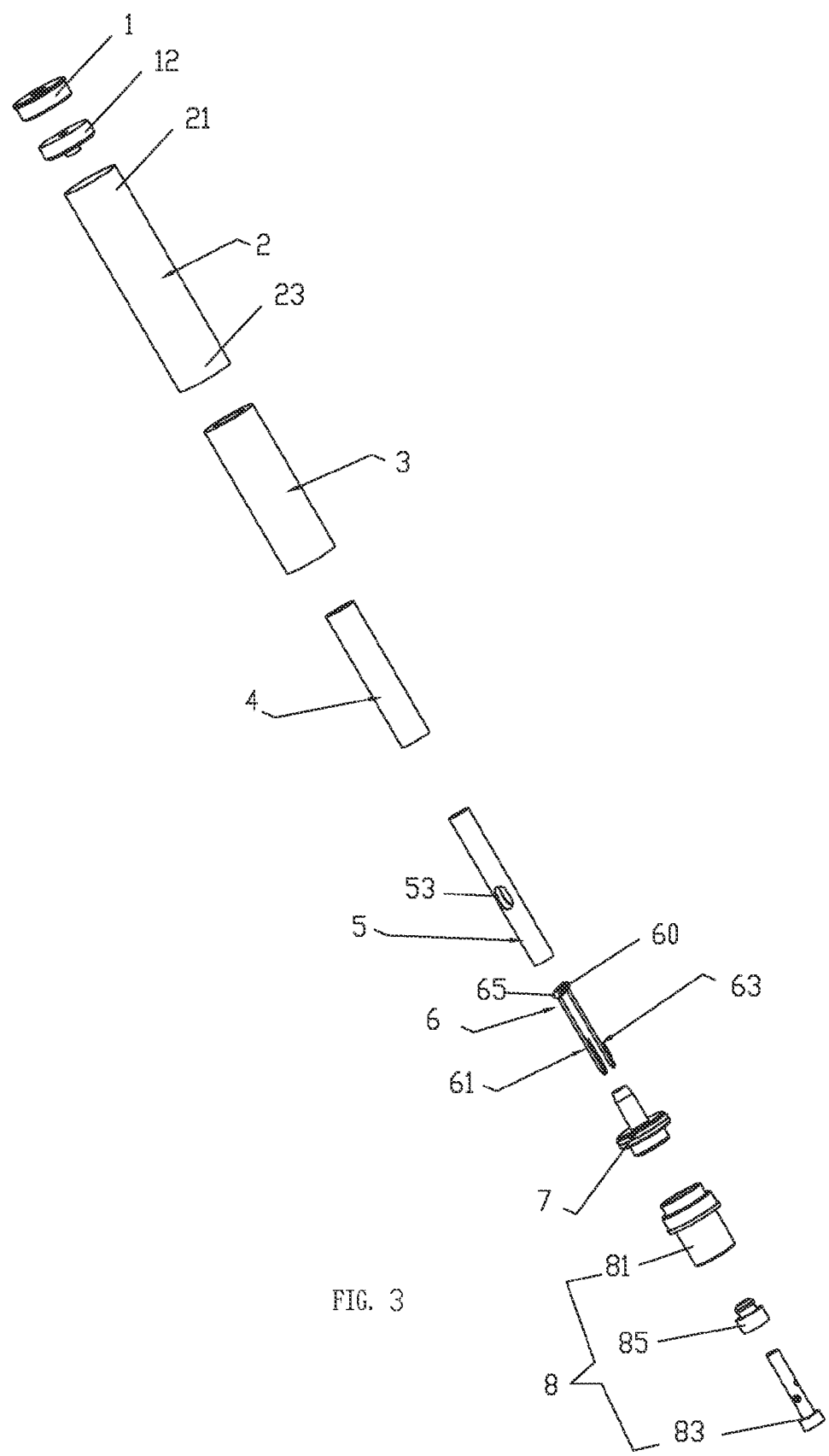
FIG. 3 is a perspective, exploded view of the atomizing device according to an embodiment of the present invention.

Referring to FIG. 1 to FIG. 3, an atomizing device 10 according to one embodiment of the present invention includes an inhalation element cover 1, an atomizing sleeve 2, a liquid storage layer 3, a cloth layer 4, a glass fiber tube 5, a heating assembly 6, an atomizing seat 7, and a connecting assembly 8. The liquid storage layer 3, the cloth layer 4, the glass fiber tube 5, and the heating assembly 6 are all assembled in the atomizing sleeve 2. The atomizing seat 7 and the connecting assembly 8 are reciprocally elastically squeezed and assembled at one end of the atomizing sleeve 2 or in the atomizing sleeve 2. The inhalation element cover 1 covers the other end of the atomizing sleeve 2. The atomizing seat 7 is an elastic atomizing seat, and defines slot 73 therein, and forms air channel 74 at a center thereof. The connecting assembly 8 includes a connecting head 81 and a top electrode 83. The connecting head 81 and the top electrode 83 is electrically insulated and assembled together. The connecting assembly 8 is inserted into the elastic atomizing seat 7 and elastically engages with the elastic atomizing seat 7 by squeezing. Concretely, the connecting head 81 is tensioningly inserted into the slot 73 of the elastic atomizing seat 7, and the top electrode 83 is tensioningly inserted into the air channel 74 of the atomizing seat 7. The atomizing seat has a higher strength after sleeved by the connecting assembly 8, which benefits to assembly of other element. The atomizing seat 7 can be better sealed at one end or inner wall of the atomizing sleeve 3.

The atomizing sleeve 2 is hollow tube-shaped in this embodiment. Two ends of the atomizing sleeve 2 are an inhalation element end 21 and a connecting end 23. The inhalation element cover 1 and the connecting assembly 8 are respectively assembled the inhalation element end 21 and the connecting end 23. The liquid storage layer 3, the cloth layer 4, the glass fiber tube 5, and the heating assembly 6 are fixed in the atomizing sleeve 2. The atomizing seat 7 is fixed and sealed in the connecting end 23 of the atomizing sleeve 2 relative to the inhalation element cover 1, and also engages with the connecting assembly 8. The inhalation element end 21 of the atomizing sleeve 2 forms a baffle ring 25 at the inner wall thereof.

The inhalation element cover 1 is adapted to the atomizing sleeve 2. The inhalation element cover 1 is ring-shaped, and may be other shaped such as circular or taper-shaped. The material and shape of the inhalation element cover 1 is adaptive to user's mouth, such as made of soft material or woody material. The center of the inhalation element cover 1 defines an air hole 11. In this embodiment, to achieve a better sealing, the inhalation element cover 1 has a sealing ring 12 formed therein, which is adapted to an inner diameter of the atomizing sleeve 2. The inhalation element cover 1 and the sealing ring 12 seals the inhalation element end 21, and all defines air holes. The center of the sealing ring 12 or the inhalation element cover 1 longitudinally extends a supporting portion 13 (13') which is inserted into the glass fiber tube 5 to support one end of the glass fiber tube 5. The center of the sealing ring 12 defines an air hole 15 to communicate with the air hole 11 of the inhalation element cover 1 and the glass fiber tube 5. The edge of the sealing ring 12 resists the baffle ring 25 of the atomizing sleeve 2, and the supporting portion 23 faces to and inserts into the center hole of the baffle ring 25.

The liquid storage layer 3 is a hollow tube in this embodiment and used to adsorb or storage tobacco flavored liquid, and located in the atomizing sleeve 2. Preferably, the liquid storage layer 3 is made of material having the function of adsorb or storage such as cotton or fiber. The liquid storage layer 3 is axially assembled in the inner wall of the atomizing sleeve 2, and two ends of the liquid storage layer 3 respectively resist the baffle ring 25 of the atomizing sleeve 25 and the atomizing seat 7.

In the embodiment, the atomizing device 10 further includes the cloth layer 4 located between the glass fiber tube 5 and the liquid storage layer 3. The cloth layer 4 may be made cotton cloth, fiber cloth, polymer cloth and so on. A main function of the cloth layer 4 is to package the glass fiber tube 5 to stably assemble the glass fiber tube 5, the heating assembly 6, the atomizing seat 7, and the connecting assembly 8 together to ensure electric circuit stably connected and reliable sealing. In addition, the function of the cloth layer 4 is to ensure the tobacco flavored liquid being conducted to the heating assembly 6 from the liquid storage layer 3 to avoid leaking of the tobacco flavored liquid along between the atomizing sleeve 2 and the connecting head 81.

The glass fiber tube 5 is hollow tube and fixed in the cloth layer 4. Correspondingly, the liquid storage layer 3 and the cloth layer 4 package on an outer of the glass fiber tube 5 to form tube. The tube wall of the glass fiber tube 5 defines an assembling hole 53 to assembly the heating assembly 6. The glass fiber tube 5 is longitudinally and axially supported in the liquid storage layer 3 and the cloth layer 4. One end of the glass fiber tube 5 is latched between the baffle ring 25 of the atomizing sleeve 2 and the supporting portion 13 of the sealing ring 12 to fix the sealing ring 12 or the inhalation element cover 1 and the glass fiber tube 5. The other end of the glass fiber tube 5 is latched in the atomizing seat 7. Preferably, the inner wall of the assembling hole 53 forms a pair of supporting ears 54 to be beneficial to support the heating assembly 6. Furthermore, to firm the glass fiber tube 5, the liquid storage layer 3 and the cloth layer 4, the glass fiber tube 5 is designed to be a double layer tube comprising an inner layer tube 51 and an outer layer tube 52. The outer layer tube 52 is further impactedly assembled on the heating assembly 6 of the inner layer tube 51. It is understood that the glass fiber tube 5 may be a single layer tube.

The heating assembly 6 includes a heating wire 60 and electronic lines 61,63 (respectively negative or positive electrode)extending from the two end of the heating wire 60. The heating wire 60 can be wrapped or folded, or other structure to contact with the liquid storage layer 3 and the cloth layer 4, used to heat and vaporize the tobacco flavored liquid. In this embodiment, the heating wire 60 is wrapped to coil-shaped, in which is inserted a liquid conducting belt or a liquid conducting post 65 to fix the heating wire 60 in the glass fiber tube 5. Two ends of the liquid conducting belt (post) 65 radially pass through the assembling hole 53 of the glass fiber tube 5 and resist to the liquid storage layer 3 so as to adsorb tobacco flavored liquid which is vaporized by the heating wire 60.

Figure 4:
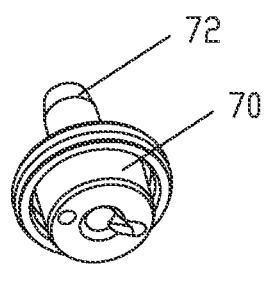
FIG. 4 is a perspective view of the atomizing seat according to an embodiment of the present invention.
Figure 5:
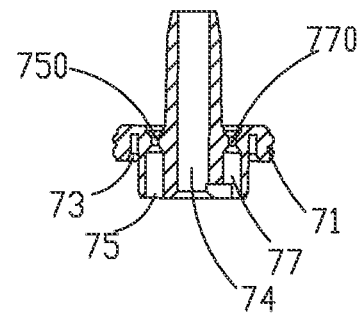
FIG. 5 is a sectional view of the atomizing seat according to an embodiment of the present invention.

Referring also to FIG. 4 to FIG. 5, the elastic atomizing seat 7 is silicon atomizing seat, and includes a main body 70 and an extending portion 72. The main body 70 is substantially column-shaped. The extending portion 72 is columnar, and axially extends a predetermined distance from the center of the main body 70. After assembly, the extending portion 72 is tightly inserted into one end of the glass fiber tube 5 away from the inhalation element cover 1. The extending portion 72 and the main body 70 cooperatively defines the central air channel 74 which communicates with outer environment and the glass fiber tube 5, thus communicates with air hole 11 of the inhalation element cover 1 and the air hole 15 of the sealing ring 12, and lastly communicates with outer environment to form air channel. The main body 70 forms an annular flange 71 on an outer edge thereof. The outer diameter of the annular flange 71 is adapted to an inner diameter of the outer sleeve 2, and to tightly latch with the inner wall of the connecting end 23 of the atomizing sleeve 2. The annular flange 71 and the outer wall of the main body 70 cooperatively restrict the slot 73 which is an annular slot. The main body 70 defines a pair of line holes 75, 77. One line hole 77 communicates with the central air channel 74. Preferably, each line hole 75, 77 is disposed to have different inner diameter at different portions thereof, and respectively has thin necks 750, 770 used for the electronic lines 61, 63 passing through and clamped by the thin neck 750, 770. In this embodiment, the main body 70 is cap-liked, and the annular flange 71 is same as to cap edge. Obviously, the main body 70 may be other shape.

Figure 6:
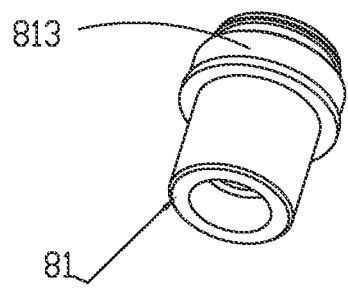
FIG. 6 is a perspective view of the connecting head according to an embodiment of the present invention.
Figure 7:
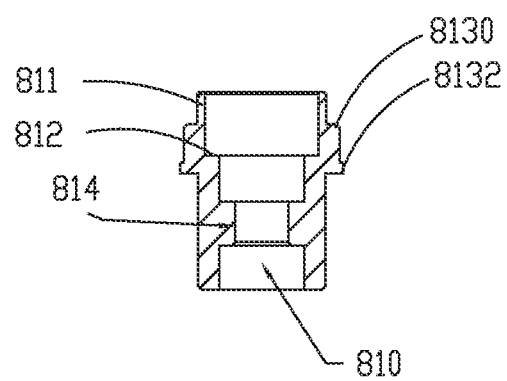
FIG. 7 is a sectional view of the connecting head according to an embodiment of the present invention.

Referring to FIG. 6 to FIG. 7, the connecting head 81 is a hard conductive element, and preferably metallic element. The top electrode 83 is inserted into the connecting head 81, and an insulating ring 85 is inserted between the top electrode 83 and the connecting head 81 to achieve insulate. The connecting head 81 is substantially hollow column and defines a stepped hole 810. The inner wall of the stepped hole 810 forms a first inner shoulder 812 and a second inner shoulder 814. One end of the connecting head 81 being inserted into the slot 73 of the atomizing seat 7 is an inserting end 811. Corresponding to a depth of the slot 73 of the atomizing seat 7 and the annular flange 71, the outer wall of the connecting head 81 spaced from the inserting end 811 a predetermined distance forms an outer annular flange 813. The inserting end 811 is inserted into the slot 73 of the atomizing seat 7 to support the elastic atomizing seat 7, so as to make the elastic atomizing seat 7 having higher strength. In one embodiment, the outer annular flange 813 may be designed to be stepped shape, and includes a first step 8130 and a second step 8132. The outer diameter of the first step 8130 is adapted to the inner diameter of the atomizing sleeve 2, and tightly latches in the connecting end 23 of the atomizing sleeve 2, and also longitudinally resists a distal end of the annular flange 71 of the atomizing seat 7. The main body 70 of the atomizing seat 7 is tensioningly inserted into the stepped hole 810 and resists the first inner shoulder 812 so as to further seal and fix the atomizing sleeve 2 and the atomizing seat 7. The edge of the connecting end 23 of the atomizing sleeve 2 resists on the second step 8132. The second inner shoulder 814 is in fact a protruding ring formed on the inner wall of the connecting head 81. The insulating ring 85 is inserted into the stepped hole 810 via another end contrary to the inserting end 811 and latches with the second inner shoulder 814. The top electrode 83 is inserted into and latches in the insulating ring 85. The top electrode 83 is long columnar, and forms a flange at a distal end thereof to latch in the insulating ring 85. The column portion of the top electrode 83 is inserted into and tensioningly fixed the central air channel 74 of the atomizing seat 7 via the connecting head 81 to further support and elastically squeeze the silicon atomizing seat 7. The side wall of the top electrode 83 and the connecting head 81 correspondingly defines air hole (not labeled), which communicates with the air channel cooperatively defined by the connecting assembly 8, the atomizing seat 7, the glass fiber tube 5, the sealing ring 12 and the inhalation element cover 1 such that the outer air is adsorbed into and adsorbed out with the smoke produced by the atomizing device 10.

Figure 8:
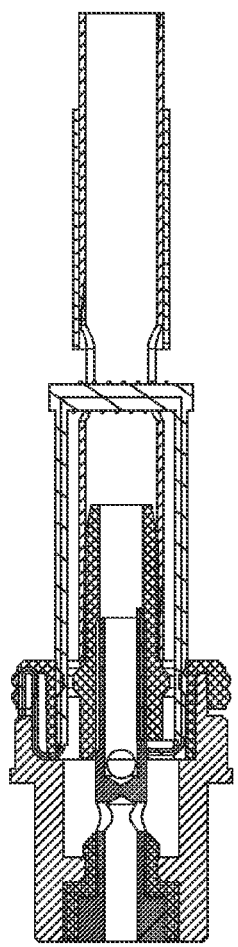
FIG. 8 is sectional view of the atomizing device in semi-finished state according to the embodiment of the present invention.

Referring to the FIG. 8 showing a semi-finished product, the heating wire 60 is fixed in the glass fiber tube 5, and the electronic lines 61, 63 pass throughout the assembling hole 50 and extend along the outer wall of the glass fiber tube 5. The two end of the liquid conducting belt (post) 65 passes throughout the assembling hole 50. At this time, the electronic lines 61, 63 respectively passes through the line holes 75, 77 of the silicon atomizing seat 7. The electronic lines 63 passes through the line hole 77 and bend into the inner wall of the central air channel 74 of the atomizing seat 7. The electronic line 61 passes through line hole 75 and then bends into the slot 73 from the edge of the main body 70. The inserting end 811 of the connecting head 81 is inserted into the slot 73 of the silicon atomizing seat 7 and tightly latches the electronic lines 61. The top electrode 83 is inserted in to the central air channel 74 of the atomizing seat 7 and tightly latches the electronic line 63. The column portion of the top electrode 83 squeezes the silicon atomizing seat 7 from the central air hole 74 of the atomizing seat 7. Therefore, the electronic lines 63 is pressed between the inner wall of the atomizing seat 7 and the outer wall of the top electrode 83, thus electrically connected with the top electrode 83. When the inserting end 811 of the metallic connecting head 81 is inserted into the slot 73 of the atomizing seat 7, the insert end 811 squeezes the annular flange 71 and the main body 70 of the atomizing seat 7 such that the electronic lines 63 is tightly latched in the slot 73 of the atomizing seat 7 and thus stably electrically connected with the metallic connecting head 81. After the metallic connecting head 81 and the top electrode 83 is inserted into the atomizing seat 7, the silicon atomizing seat 7 is elastically pressed inwards to further latch the electronic lines 61, 63 passing through the line holes 75, 77, especially latch in the thin necks 750,770. Therefore, the electronic lines 61, 63 cannot be pulled. Simultaneously, the annular flange 71 of the silicon atomizing seat 7 is pressed outwards and expands so as to evenly latch in the inner wall of the atomizing sleeve 2, thus achieve better sealing effect. Furthermore, after the connecting head 81 and the top electrode 83 are inserted into the silicon atomizing seat 7, the total hardness and strength of the atomizing device is enhanced. Thus, it is convenient to hold the connecting head 81 to package the cloth layer 4 and the liquid storage layer 3 on the glass fiber tube 5. The liquid storage layer 3 of the embodiment is made of packaging cotton. The assembly is convenient. After packaging the cloth layer 4 and the liquid storage layer 3 on the glass fiber tube 5, the atomizing sleeve is packaged on the glass fiber tube 5. Then the inhalation element end 21 is inserted into the sealing ring 12 and the inhalation element cover 1. Thus the atomizing device 10 is completely assembled. With the aid of elastic engagement between the metallic connecting head 81, the top electrode 83 and the silicon atomizing seat 7, the electronic lines 61, 63 of the atomizing device 10 according to the present invention is tightly pressed in, and stably electrically connected with the metallic connecting head 81 and the top electrode 83, which needs no any welding, saves costs, and avoids producing any harmful matter. In addition, the silicon atomizing seat 7 is sleeved in the connecting assembly 8, and is pressed to expand outwards to make the atomizing seat 7 sealed in the atomizing sleeve 2 and does not deform and slide.

Figure 9:
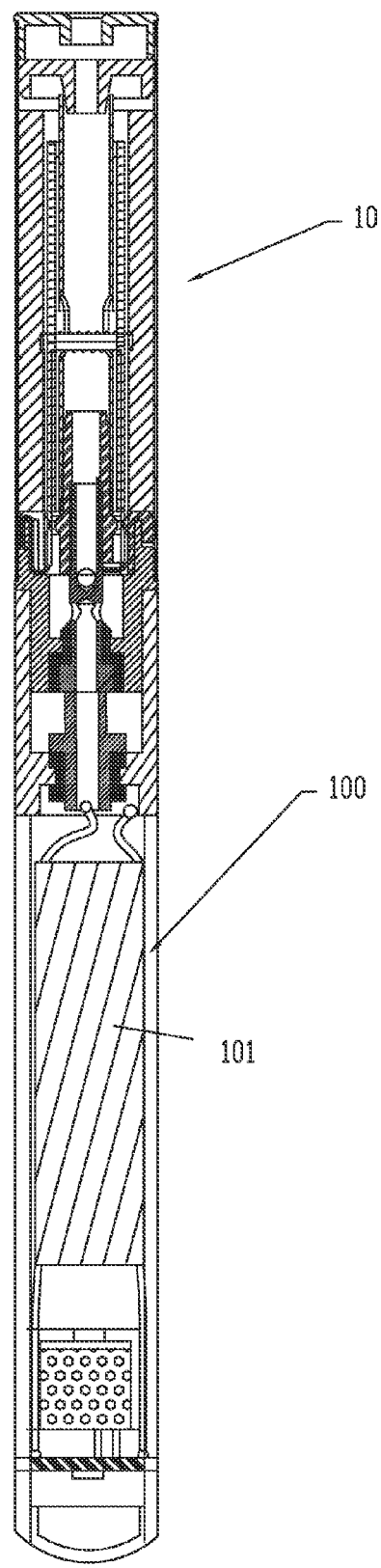
FIG. 9 is sectional view of the electronic cigarette according to an embodiment of the present invention.

Referring to FIG. 9, the electronic cigarette according to the present invention includes the atomizing device 10 and a power source pole 100. The atomizing device 10 and the power source pole 100 are detachably or undetachably connected together. The power source pole 100 includes battery 101 disposed therein. One end of the power source pole 100 is adapted for a connecting end of the atomizing device 10, and may connect with the connecting end of the atomizing device 10 by thread connection, latching connection, tensioning connection, adhesive bonding, or integrally molding. In use, the power source pole 100 connects with the atomizing device 10, and the top electrode 83 and the metallic connecting head 81 are respectively connected with the positive and negative electrode of the power source pole 100 so as to supply power to the heating wire 60.

Figure 10:
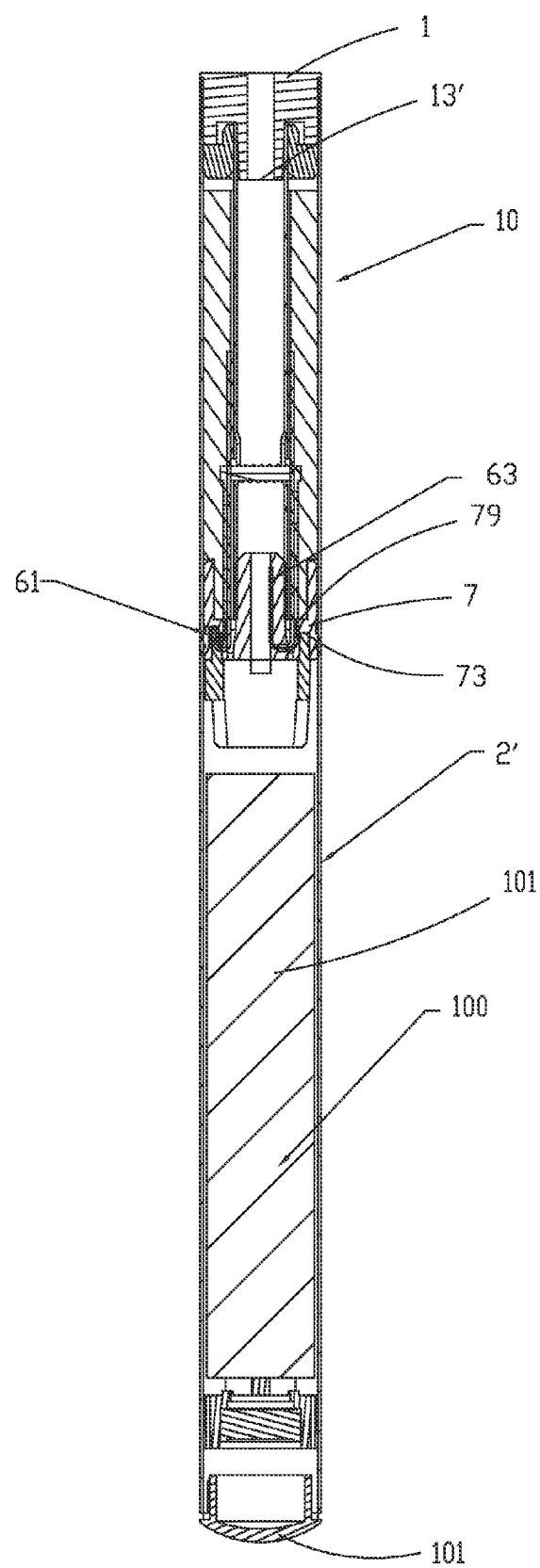
FIG. 10 is sectional view of the electronic cigarette according to the another embodiment of the present invention.

Referring to FIG. 10, a disposable electronic cigarette 100 is shown. The atomizing sleeve 2 comprises the continuous outer sleeve 2' of the electronic cigarette 100. The disposable electronic cigarette 100 is divided into two sections. One section is corresponding to the atomizing device 10, and the other section is corresponding to the power source pole 100. The assembling of each section is same as the above. The difference is that the atomizing seat 7 and the connecting assembly 8 are assembled in the outer sleeve 2', instead of being assembled in the distal end. The battery 101 is located in the outer sleeve 2' and engages with the connecting assembly 8. The positive and negative electrodes of a power supply source are respectively electrically connected with the connecting head 81 and the electronic lines 61 63 of the heating assembly 6, thus to achieve electrical connection to the electronic lines 61, 63 of the heating assembly 6. The outer sleeve 2' has a battery cover 103 disposed at the other end thereof contrary to the inhalation element cover 1. In the disposable electronic cigarette 100, the positive and negative electrodes of the battery respectively electrically connected with the electronic lies 61, 63 of the heating assembly 6, thus the top electrode 83 may be omitted.

Referring also to FIG. 10, the inhalation element cover 1 and the sealing ring 12 are latched each other, and an extending portion 13' inserting into the glass fiber tube 5 may be designed to axially extend from the inhalation element cover 1. The silicon atomizing seat 7 may be designed to have H-shaped cross-section, thus form the slots 73, 79 at two ends thereof. The slot 79 is used to latch one inserting end of the glass fiber tube 5 so as to further fix and position.

It is understood that the electronic cigarette may be reusable electronic cigarette. The atomizing device 10 and the power source pole 100 may be undetachably connected together. The atomizing device 10 may have liquid cup to storage tobacco flavored liquid or other liquid matter. In other embodiment, tobacco flavored liquid may be repeatedly added. For example, the inhalation element cover 1 and the sealing ring 12 are configured to be removable structure to repeatedly pour into the tobacco flavored liquid.

The cloth layer 4 of the embodiment according to the present invention may be omitted according concrete requirements, or be replaced by other material. In addition, the heating wire 6 of the heating assembly 6 may be other heating element such as heating block, heating stick, or other heating ways. The electronic lines 61, 63 connected to the two ends of the heating element pass through and is tensioningly fixed in the elastic atomizing seat 7, and then electrically connects with the connecting assembly 8.

The above-mentioned is embodiments of the present invention. It is pointed out that various improvements and modifications can be made to the embodiments by those skilled in the art without departing from the true spirit and scope of the disclosure as defined by the appended claims.

What is claimed is:

1. An atomizing device, comprising an outer sleeve, a liquid storage layer, a heating assembly, an atomizing seat and a connecting assembly, the liquid storage layer, the heating assembly and the atomizing seat being assembled in the outer sleeve; wherein the atomizing seat is an elastic atomizing seat, the connecting assembly is inserted in the elastic atomizing seat to elastically squeeze and tensioningly engage with the elastic atomizing seat;

the connecting assembly comprises a conductive connecting head and a top electrode, the conductive connecting head and the top electrode are insulatively engaged with each other; the elastic atomizing seat defines a slot, and the conductive connecting head is tensioningly inserted into the slot; the elastic atomizing seat defines an air channel therein, and the top electrode is inserted into the air channel to tensioningly engage with the inner wall of the elastic atomizing seat;

the heating assembly comprises a heating element and two electronic lines respectively connected to two ends of the heating element; one electronic line is tensioningly fixed between the elastic atomizing seat and the connecting head to electrically connect to the connecting head; the other electronic line is tensioningly fixed between the air channel wall of the elastic atomizing seat and the top electrode to electrically connect to the top electrode; and the conductive connecting head is metallic.

2. The atomizing device defined according to claim 1, wherein the elastic atomizing seat is adapted for the outer sleeve, and the elastic atomizing seat is elastically expanded as a result of the connecting assembly being inserted in the elastic atomizing seat to be tightly sealed in the inner wall of the outer sleeve.

3. The atomizing device defined according to claim 1, wherein the elastic atomizing seat comprises a main body and an axial extending portion formed on a center of the main body; the air channel of the atomizing seat runs through the main body and the axial extending portion; the main body forms an annular flange on an outer edge thereof; the outer diameter of the annular flange is adapted to an inner diameter of the outer sleeve, and tightly latches the inner wall of the outer sleeve to achieve seal; and the annular flange and the outer wall of the main body cooperatively define the slot.

4. The atomizing device defined according to claim 3, wherein the outer wall of the connecting head forms an annular flange adapted to the inner diameter of the outer sleeve, and the connecting head forms a stepped hole therein; when the connecting head is inserted into the slot, the annular flange of the connecting head longitudinally resists the annular flange of the atomizing seat, and the main body of the atomizing seat is tensioningly latched in the stepped hole of the connecting head; the top electrode is latched the stepped hole of the connecting head via an insulating ring, and longitudinally extends and tensioningly latches in the inner wall of the air channel of the main body of the atomizing seat.

5. The atomizing device defined according to claim 1, wherein the elastic atomizing seat forms a pair of line holes used for the electronic lines passing through; each of the line holes has a thin neck, when the atomizing seat is squeezed, the thin neck elastically deforms to tightly clamp the electronic lines therein.

6. The atomizing device defined according to claim 5, wherein the line holes longitudinally pass through the main body of the elastic atomizing device, and one line hole communicates with the air channel; one electronic line passes through a corresponding line hole and bypasses a bottom edge of the main body to stretch into the slot and is latched in the inner wall of the slot by the connecting head; the other electronic line passes through the other corresponding line hole to go back the inner wall of the air channel and is clamped by the top electrode.

7. The atomizing device defined according to claim 1, wherein the atomizing device further comprises a glass fiber tube; the glass fiber tube defines assembling holes to fix the heating assembly; the glass fiber tube is a double-layer tube; an inner layer tube of the glass fiber tube forms a supporting ear corresponding to the assembling hole to fix the heating assembly; and the elastic atomizing seat is made of silicone.

8. The atomizing device defined according to claim 7, wherein the liquid storage layer is cotton packaging on an outer of the glass fiber tube for storing liquid.

9. The atomizing device defined according to claim 8, wherein the glass fiber tube is packaged by a cloth layer, and then is packaged by the storage cotton.

10. An electronic cigarette, comprising an atomizing device and a battery assembly, the atomizing device comprising an outer sleeve, liquid storage layer, a heating assembly, an atomizing seat and a connecting assembly, the liquid storage layer, the heating assembly and the atomizing seat being assembled in the outer sleeve, wherein the atomizing seat is an elastic atomizing seat, the connecting assembly is inserted in the elastic atomizing seat to elastically squeeze and tensioningly engage with the elastic atomizing seat, positive and negative electrodes of the battery assembly respectively electrically connect with the connecting assembly;

the connecting assembly comprises a conductive connecting head and a top electrode, the conductive connecting head and the top electrode are insulatively engaged with each other; the elastic atomizing seat defines a slot, and the conductive connecting head is tensioningly inserted into the slot; the elastic atomizing seat defines an air channel therein, and the top electrode is inserted into the air channel to tensioningly engage with the inner wall of the elastic atomizing seat;

the heating assembly comprises a heating element and two electronic lines respectively connected to two ends of the heating element; one electronic line is tensioningly fixed between the elastic atomizing seat and the connecting head to electrically connect to the connecting head; the other electronic line is tensioningly fixed between the air channel wall of the elastic atomizing seat and the top electrode to electrically connect to the top electrode; and the conductive connecting head is metallic.

11. The electronic cigarette defined according to claim 10, wherein the battery assembly is assembled in the outer sleeve.

12. The electronic cigarette defined according to claim 10, wherein the elastic atomizing seat is adapted for the outer sleeve, the elastic atomizing seat is elastically expanded as a result of the connecting assembly being inserted in the elastic atomizing seat to be tightly sealed in the inner wall of the outer sleeve.

13. An electronic cigarette comprising an atomizing device, and a power source pole, the power source pole connecting with the atomizing device, the atomizing device comprising an outer sleeve, a liquid storage layer, a heating assembly, an atomizing seat and a connecting assembly, the liquid storage layer, the heating assembly and the atomizing seat being assembled in the outer sleeve, wherein the atomizing seat is an elastic atomizing seat, the connecting assembly is inserted in the elastic atomizing seat to elastically squeeze and tensioningly engage with the elastic atomizing seat, positive and negative electrodes of the power source pole respectively electrically connect with the connecting assembly;

the connecting assembly comprises a conductive connecting head and a top electrode, the conductive connecting head and the top electrode are insulatively engaged with each other; the elastic atomizing seat defines a slot, and the conductive connecting head is tensioningly inserted into the slot; the elastic atomizing seat defines an air channel therein, and the top electrode is inserted into the air channel to tensioningly engage with the inner wall of the elastic atomizing seat;

the heating assembly comprises a heating element and two electronic lines respectively connected to two ends of the heating element; one electronic line is tensioningly fixed between the elastic atomizing seat and the connecting head to electrically connect to the connecting head; the other electronic line is tensioningly fixed between the air channel wall of the elastic atomizing seat and the top electrode to electrically connect to the top electrode; and the conductive connecting head is metallic.

14. The electronic cigarette defined according to claim 13, wherein the elastic atomizing seat is adapted for the outer sleeve, the elastic atomizing seat is elastically expanded as a result of the connecting assembly being inserted in the elastic atomizing seat to be tightly sealed in the inner wall of the outer sleeve.

* * * * *